United States Patent [19]

Merz et al.

[11] Patent Number: 5,240,933
[45] Date of Patent: Aug. 31, 1993

[54] 14-HYDROXY-N-(2-METHOXYETHYL)-7,8-DIHYDROMORPHINE AND -NORISOMORPHINE, PROCESSES FOR THE PREPARATION THEREOF AND THE USE THEREOF AS PHARMACEUTICAL COMPOSITIONS

[75] Inventors: Herbert Merz, Ingelheim am Rhein; Ingrid Wiedemann, Wiesbaden; Helmut Ensinger, Ingelheim am Rhein; Klaus Stockhaus, Bingen; Matthias Grauert, Ingelheim am Rhein, all of Fed. Rep. of Germany

[73] Assignee: Boehringer Ingelheim GmbH, Ingelheim am Rhein, Fed. Rep. of Germany

[21] Appl. No.: 951,289

[22] Filed: Sep. 25, 1992

[30] Foreign Application Priority Data

Sep. 27, 1991 [DE] Fed. Rep. of Germany ....... 4132159

[51] Int. Cl.$^5$ ................ C07D 489/08; A61K 31/485
[52] U.S. Cl. ..................................... 514/282; 546/44
[58] Field of Search ........................... 546/44; 514/282

[56] References Cited

PUBLICATIONS

Ronai et al, The Journal of Pharmacology & Experimental Therapeutics (vol. 200 Jan.–Mar. 1977) "Orientation of the Oxygen Atom at C-6 as a Determinant of Agonistic Activity in the Oxymorphone Series".

Pollock, Life Sciences (vol. 17, pp. 465–476) "Dihydromorphinone Ketone Reductases".

Chatterjie et al. Journal of Medicinal Chemistry (vol. 18, No. 5, May 1975) "Stereospecific Synthesis of the 6$\beta$-Hydroxy Metabolites of Naltrexone and Naloxone".

Malspeis et al. Research Communications in Chemical Pathology and Pharmacology (vol. 12, No. 1, Sep. 1975) "Metabolic Reduction of Naltrexone I. Synthesis, Separation & Characterization of Naloxone and Naltrexone Reduction Products & Qualitative Assay of Urine and Bile Following Administration of Naltrexone, $\alpha$–Naltrexol, or $\beta$–Naltrexol".

Hahn et al. The Journal of Organic Chemistry (vol. 40, No. 1, Jan. 1975) "Narcotic Antagonists. V. Stereochemisry of Reactions at C-6 in 14–Hydroxynoroxymorphone Derivatives".

Chemical Abstracts (vol. 62, No. 5, Mar. 1965) Abstract No. 5308h "Derivatives of Morphine. IV. 14–Hydroxymorphine and 14–Hydroxydihydromorphine".

Primary Examiner—Donald G. Daus
Attorney, Agent, or Firm—D. E. Frankhouser; A. R. Stempel; M-E. M. Timbers

[57] ABSTRACT

The present invention relates to 14-hydroxy-N-(2-methoxyethyl)-7,8-dihydromorphine and -norisomorphine, processes for preparing them and their use as pharmaceutical compositions.

6 Claims, No Drawings

14-HYDROXY-N-(2-METHOXYETHYL)-7,8-DIHYDROMORPHINE AND -NORISOMORPHINE, PROCESSES FOR THE PREPARATION THEREOF AND THE USE THEREOF AS PHARMACEUTICAL COMPOSITIONS

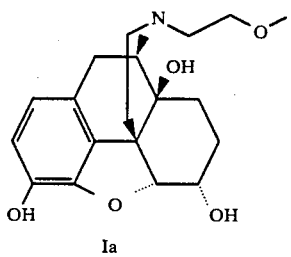

Ia

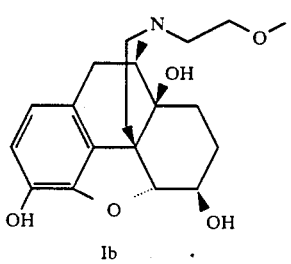

Ib

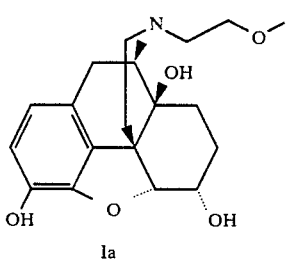

Ia

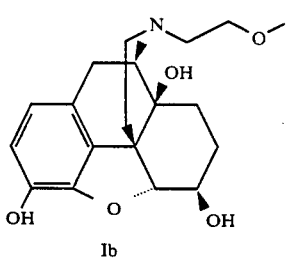

Ib

The present invention relates to the epimeric compounds of general formulae Ia and Ib, namely 14-hydroxy-N-(2-methoxyethyl)-7,8-dihydromorphine (Ia) and 14-hydroxy-N-(2-methoxyethyl)-7,8-dihydronoriso-morphine(Ib), processes for preparing them and their use as pharmaceutical compositions.

The invention further relates to the corresponding physiologically suitable acid addition salts with organic or inorganic acids. Preferred salts are, for example, those with hydrochloric acid, hydrobromic acid, sulphuric acid, phosphoric acid, methanesulphonic acid, ethanesulphonic acid, toluenesulphonic acid, benzenesulphonic acid, lactic acid, malonic acid, succinic acid, maleic acid, fumaric acid, malic acid, tartaric acid, citric acid or benzoic acid.

The compounds according to the invention and the acid addition salts thereof have valuable pharmacological properties and have a therapeutically useful effect on the central nervous system and can be used as non-addictive analgesics in pain control.

The analgesic effect of the compounds according to the invention can be demonstrated by the phenylquinone writhing test which was carried out in accordance with S. Irwin [Psychopharmacologia 13, 222 to 257 (1968)]. In this test, compound Ia according to the invention has a mean effective dose (MED) of 2.5 mg/kg p.o. (64% effect) and compound Ib according to the invention has an MED of 10 mg/kg p.o. (71% effect). Ibuprofen as a comparison compound, has an effect of 65% in a dose of 25 mg/kg p.o. In the opiate receptor binding test with [$^3$H]-naloxon as radioligand, Ia has a $K_i$ of 2.14 nM and with the addition of 0.1M sodium chloride it has a $K_i$ of 2.39 nM, corresponding to a sodium shift of 1.12. In these two binding tests, compound Ib has a $K_i$ value of 1.07 nM and 1.19 nM, respectively (sodium shift: 1.11). This small sodium shift indicates the antagonistic nature of the compounds according to the invention. In the opiate receptor binding test with [$^3$H]-dihydromorphine as radioligand, Ia has a $K_i$ of 0.91 nM and Ib has a $K_i$ of 1.79 nM.

The compounds according to the invention can be prepared by various methods known per se by reduction of N-(2-methoxyethyl)-noroxymorphone.

The preparation of this noroxymorphone derivative is known from German Offenlegungsschrift 32 20 831.

The reduction of the N-(2-methoxyethyl)-noroxymorphone-hydrochloride is carried out by methods known per se (from the prior art) [R. C. Larock, Comprehensive Organic Transformations, A Guide to Functional Group Preparations, VCH Verlagsgesellschaft m.b.H., Weinheim, 1989, page 527 ff and loc. cit.; J. March, Advanced Organic Chemistry, J. Wiley & Sons, New York, 1985, page 809 and loc. cit.; C. Ferri, Reaktionen der organischen Synthese, Georg Thieme Verlag, Stuttgart 1978, pages 102, 108, 115 and loc. cit.].

It is preferred to carry out reduction with complex alkali boron or alkali aluminium hydrides, optionally in the presence of a catalyst [A. Hajos, Complex Hydrides, Elsevier, New York 1979; H. O. House, Modern Synthetic Reactions, 2nd ed., W. A. Benjamin, New York, 1972, p. 49 ff.; O. H. Wheeler in Patai, The Chemistry of the Carbonyl Group, part 1, Interscience, New York, 1966, p. 507 ff., H. C. Brown, J. Chem. Educ. 38 (1961) 173; E. Schenker, Angew. Chem. 73 (1961) 81; E. Schenker, Newer Methods Prep. Org. Chem. 4 (1968) 196].

Sodium tetrahydridoboranate (sodium boronhydride) and lithium tetrahydridoalanate are particularly preferred as reducing agents.

Any inert solvent which does not change under the reaction conditions specified is suitable for performing the reduction. Examples include ethers such as di-n-butylether, glycoldimethylether(glyme), diglycoldimethylether(diglyme), cyclic ethers such as dioxane and tetrahydrofuran and—provided that the reducing agent used permits—preferably alcohols such as methanol, ethanol, isopropanol or glycol, a mixture of ethanol and sodium hydroxide solution being particularly preferred. It is also possible to use mixtures of the above-mentioned solvents.

The reduction itself is carried out at a temperature in the range from −10° C. to the boiling point of the reaction mixture, preferably between −5° and 40° C. and particularly between 0° and 30° C.

In order to perform the reduction, in a preferred embodiment the N-(2-methoxyethyl)-noroxymorphone hydrochloride is dissolved in a mixture of ethanol and sodium hydroxide solution and the reducing agent, which is preferably sodium borohydride, is added thereto. After the reduction has ended and the reaction products have been isolated they are purified by column chromatography, separated into the two epimers and isolated.

Another preferred embodiment consists of a catalytic reduction with hydrogen. The carrying out of catalytic reduction of this kind is known from the prior art [P. N. Rylander, "Catalytic Hydrogenation over Platinum Metals", Academic Press, New York, 1967, p. 238]. Preferably, Raney nickel is used as catalyst [J. A. Schreifels, P. C. Maybury and W. E. Swartz Jr., J. Org. Chem. 46 (1981) 1263].

In the reduction reactions mentioned above, mixtures of the two epimers are obtained. By contrast, if formamidinesulphinic acid is used [N. Chatterjie and H. Blumberg, J. Med. Chem. 18 (1975) 490] as reducing agent, the β-epimer can be targeted.

The Examples which follow are intended to illustrate the invention without restricting it to the scope of the Examples:

EXAMPLES 1) 7.64 g (0.02 mol) of N-(2-methoxyethyl)-noroxymorphone-hydrochloride are suspended in 150 ml of ethanol and 10.5 ml of 2N sodium hydroxide solution are added with stirring, to form a solution. As stirring is continued, 0.41 g of 98% (0.01 mol) sodium borohydride are added. The mixture is stirred for a further hour at ambient temperature and 50 ml of water are added. Then the solvent is drawn off in vacuo to leave a residue of about 60 g which is left to crystallise for 2 hours in an ice bath. The crystals precipitated are suction filtered, washed three times with 10 ml of water and then dried. The mother liquor is concentrated down to about 30 g and crystallised once more whilst cooling with ice. The crystals are suction filtered, washed with water and dried.

The crystals are separated into the two epimers by column chromatography on 1 kg of silica gel (MN K 60, 230-400 mesh ASTM made by Macherey and Nagel) using a mixture of chloroform, methanol and conc. ammonia (90:10:0.5) as eluant. The suitable fractions are evaporated down in vacuo and the residue is recrystallised from ethanol. 1.88 g (27%) of 14-hydroxy-N-(2-methoxyethyl)-7,8-dihydronormorphine (α-epimer) is obtained as the faster running isomer, m.p. 192°–194° C. and 1.13 g (16%) of 14-hydroxy-N-(2-methoxyethyl)-7,8-dihydronorisomorphine (β-epimer) are obtained, m.p. 201°–203° C. The two epimers have the following rotary values:

$[\alpha]_D^{25}$ (α-epimer): −155.3°, (c=1, CH$_3$OH/1N HCl, 1:1) and $[\alpha]_D^{25}$ (β-epimer): −130.2° (c=1, CH$_3$OH/1N HCl 1:1).

2) 7.64 g (0.02 mol) of N-(2-methoxyethyl)-noroxymorphone hydrochloride are dissolved in 400 ml of water under a nitrogen atmosphere and 11 ml of 2N sodium hydroxide solution are added with stirring. A clear solution is obtained, to which is added a solution of 8.64 g (0.08 mol) of formamidinesulphinic acid in 70 ml of 2N sodium hydroxide solution. The mixture is then stirred for 1 hour at 85° C., cooled to ambient temperature and mixed with 5 drops of conc. hydrochloric acid and a solution of 10 g of sodium carbonate and 10 g of sodium hydrogen carbonate in 100 ml of water. The aqueous phase is extracted six times with 150 ml of dichloromethane. The combined organic extracts are dried and the solvent is removed in vacuo after the drying agent has been filtered off. The residue is recrystallised from about 100 ml of ethanol. In this way, 5.0 g (72%) of the 14-hydroxy-N-(2-methoxyethyl)-7,8-dihydronoriso-morphine (β-epimer) are obtained, m.p.: 201° C.

The present invention also includes pharmaceutical preparations which contain one or more compounds according to the invention in addition to non-toxic, inert, pharmaceutically acceptable carriers, or which consist of one or more active substances according to the invention, as well as methods of preparing these preparations.

The present invention also includes pharmaceutical preparations in dosage units. This means that the preparations are presented in the form of individual items, e.g. plain or coated tablets, capsules, pills, suppositories and ampoules, the active substance content of which corresponds to a fraction or a multiple of a single dose. The dosage units may contain, for example, 1, 2, 3 or 4 single doses or ½, ⅓ or ¼ of a single dose. A single dose preferably contains the amount of active substance administered in one application and generally corresponds to all, half or a third or a quarter of a daily dose.

The phrase "non-toxic, inert, pharmaceutically acceptable carriers" indicates solid, semisolid or liquid diluents, fillers and formulation excipients of every kind.

Examples of preferred pharmaceutical preparations are plain and coated tablets, capsules, pills, granules, suppositories, solutions, suspensions and emulsions.

Plain and coated tablets, capsules, pills and granules may contain the active substance or substances in addition to the usual carriers such as (a) fillers and extenders, e.g. starches, lactose, sucrose, glucose, mannitol and silicic acid, (b) binders, e.g. carboxymethylcellulose, alginates, gelatines, polyvinylpyrrolidone, (c) moistening agents, e.g. glycerol, (d) disintegrants, e.g. agar-agar, calcium carbonate and sodium carbonate, (e) solution retardants, e.g. paraffin and (f) resorption accelerators, e.g. quaternary ammonium compounds, (g) wetting agents, e.g. cetyl-alcohol, glycerol monostearate, (h) adsorption agents, e.g. kaolin and bentonite and (i) lubricants such as talc, calcium and magnesium stearate and solid polyethyleneglycols or mixtures of the substances listed under (a) to (i).

The plain and coated tablets, capsules, pills and granules may be provided with the conventional coatings and shells optionally containing opacifiers and may also be constituted so that they release the active substance or substances only or preferably in a certain part of the intestinal tract, optionally after a period of delay, whilst polymer substances and waxes, for example, may be used as the embedding compositions.

The active substance or substances may optionally be presented in the form of macrocapsules with one or more of the carriers mentioned above.

Suppositories may contain, in addition to the active substance or substances, the usual water soluble or water insoluble carriers, e.g. polyethyleneglycols, fats, e.g. cocoa butter and higher esters (e.g. $C_{14}$-alcohol with $C_{15}$-fatty acid) or mixtures of these substances.

Solutions and emulsions may contain in addition to the active substance or substances the usual carriers such as solvents, solubilisers and emulsifiers, e.g. water, ethyl alcohol, isopropyl alcohol, ethylcarbonate, ethyl acetate, benzyl alcohol, benzylbenzoate, propyleneglycol, 1,3-butyleneglycol, dimethylformamide, oils, particularly cotton seed oil, groundnut oil, corn oil, olive oil, castor oil and sesame seed oil, glycerol, glycerolformal, tetrahydrofuryl alcohol, polyethyleneglycols and fatty acid esters of sorbitane or mixtures of these substances.

For parenteral use the solutions and emulsions may also be presented in sterile and blood-isotonic form.

Suspensions may contain, in addition to the active substance or substances, the usual carriers such as liquid diluents, e.g. water, ethyl alcohol, propyleneglycol, suspension agents, e.g. ethoxylated isostearyl alcohols, polyoxyethylene sorbitol and sorbitane esters, microcrystalline cellulose, aluminium methahydroxide, bentonite, agar-agar and gum tragacanth or mixtures of these substances.

The presentation forms described above may also contain colourings, preservatives and additives for improving smell and flavour, e.g. peppermint oil and eucalyptus oil and sweeteners such as saccharin.

The therapeutically effective compounds should preferably be present in the above-mentioned pharmaceutical preparations in a concentration of about 0.1 to 99.5, preferably about 0.5 to 95% by weight of the total mixture.

The pharmaceutical compositions mentioned above may also contain other pharmaceutically active substances in addition to the compounds according to the invention.

The pharmaceutical preparations mentioned above are prepared in the usual way by known methods, e.g. by mixing the active substance or substances with the carrier or carriers.

The preparations described may be administered by oral, rectal, parenteral (intravenous, intramuscular, subcutaneous) route. Suitable preparations include injectable solutions, solutions and suspensions for therapeutic use.

In human medicine it has generally proved advantageous to administer the active substance or substances according to the invention in total amounts of about 0.5 to about 500, preferably 5 to 100 mg/kg of body weight in 24 hours, optionally in the form of several single doses, to achieve the desired results. A single dose contains the active substance or substances according to the invention preferably in amounts from about 1 to about 80, more particularly 3 to 30 mg/kg of body weight. However, it may be necessary to deviate from the dosages specified, depending on the nature and body weight of the patient, the nature and gravity of the disease, the type of preparation and method of administering the drug as well as the length of time or interval within which the drug is administered.

Thus, it may be sufficient in some cases to use less than the amount of active substance specified above, whereas in other cases the amount specified must be exceeded. The optimum dose and method of administration of the active substances can readily be determined by the person skilled in the art on the basis of their expert knowledge.

The Examples of preparations which follow are intended to illustrate the invention without restricting it:

| 1. Tablets | |
|---|---|
| The tablet contains the following ingredients: | |
| Active substance according to formula I | 0.020 parts |
| Stearic acid | 0.010 parts |
| Dextrose | 1.890 parts |
| Total | 1.920 parts |

Method of preparation

The substances are mixed together in a known manner and the mixture is compressed to form tablets, each weighting 1.92 g and containing 20 mg of active substance.

2. Ointment

The ointment is made up of the following ingredients:

| Active substance according to formula I | 10 mg |
|---|---|
| Neribas ointment (brand name Scherax) ad | 10 g |

Method of preparation

The active substance is triturated with 0.5 g of ointment base and the remaining base is gradually added in amounts of 1.0 g to form an ointment. A 0.5% ointment is obtained. The distribution of the active substance in the base is optically monitored under the microscope.

| 3. Cream | |
|---|---|
| Composition: | |
| Active substance according to formula 1 | 50 mg |
| Neribas ointment (brand name Scherax) ad | 10 g |

Method of preparation

The active substance is triturated with 0.5 g of cream base and the remaining base is gradually incorporated in amounts of 1.0 g using a pestle. A 0.5% cream is obtained. The distribution of the active substance in the base is optically monitored under the microscope.

| 4. Ampoule solution | |
|---|---|
| Composition: | |
| Active substance according to formula 1 | 1.0 mg |
| Sodium chloride | 45.0 mg |
| Water for injections ad | 5.0 ml |

Method of preparation

The active substance is dissolved in water at its own pH or optionally at pH 5.5 to 6.5 and sodium chloride is added to make the solution isotonic. The resulting solution is filtered free from pyrogens and the filtrate is transferred under aseptic conditions into ampoules which are then sterilised and sealed by fusion. The ampoules contain 1 mg, 5 mg and 10 mg of active substance.

5. Suppositories

Each suppository contains:

| | |
|---|---|
| Active substance according to formula 1 | 1.0 parts |
| Cocoa butter (melting point: 36-37° C.) | 1200.0 parts |
| Carnauba wax | 5.0 parts |

METHOD OF PREPARATION

The cocoa butter and carnauba wax are melted together. At 45° C. the active substance is added and the mixture is stirred to produce a complete dispersion. The mixture is poured into suitably sized moulds and the suppositories are packaged appropriately.

What is claimed is:

1. A compound of formula Ia

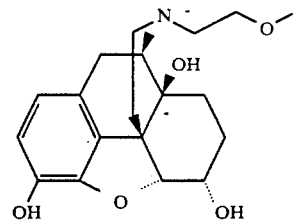

2. A compound of formula Ib

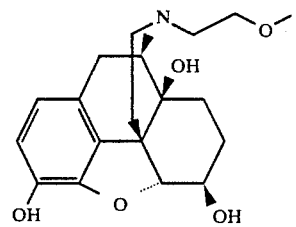

3. A pharmaceutical composition of matter comprising a compound as recited in claim 1 and a pharmaceutically acceptable carrier.

4. A pharmaceutical composition of matter comprising a compound as recited in claim 2 and a pharmaceutically acceptable carrier.

5. A method of relieving pain in a warm-blooded animal which comprises administering to said animal a therapeutically effective amount of a compound as recited in claim 1.

6. A method of relieving pain in a warm-blooded animal which comprises administering to said animal a therapeutically effective amount of a compound as recited in claim 2.

* * * * *